United States Patent [19]
McCarty

[11] Patent Number: 5,789,401
[45] Date of Patent: Aug. 4, 1998

[54] HIGH-DOSE CHROMIUM/BIOTIN TREATMENT OF TYPE II DIABETES

[75] Inventor: Mark F. McCarty, San Diego, Calif.

[73] Assignee: Nutrition 21, San Diego, Calif.

[21] Appl. No.: 908,819

[22] Filed: Aug. 8, 1997

[51] Int. Cl.$^6$ .................. A61K 31/555; A61K 31/415
[52] U.S. Cl. ........................... 514/188; 514/387
[58] Field of Search ..................... 514/186, 387

[56] References Cited

U.S. PATENT DOCUMENTS

| | | | |
|---|---|---|---|
| 4,315,927 | 2/1982 | Evans | 424/245 |
| 5,087,623 | 2/1992 | Boynton et al. | 514/188 |

FOREIGN PATENT DOCUMENTS

| | | | |
|---|---|---|---|
| WO 96/35421 | 11/1996 | WIPO | 514/188 |

OTHER PUBLICATIONS

Coggeshall, J., et al. (1985) Biotin status and plasma glucose in diabetics. Ann. N.Y. Acad. Sci. 447:387–392.

Maebashi, M., et al. (1993) Therapeutic evaluation of the effect of biotin on hyperglycemia in patients with non–insulin dependent diabetes mellitus. J. Clin. Biochem. Nutr. 14:211–218.

Mock, D. in Present Knowledge in Nutrition, seventh edition, Chapter 22, pp. 220–235

Reddi, A., et al. (1988) Biotin supplementation improves glucose and insulin tolerances in genetically diabetic kk mice. Life Sciences 42: 1323–1330.

Zhang, H., et al. (1996) A high biotin improves the impaired glucose tolerance of long–term spontaneously hyperglycemic rats with non–insulin–dependent diabetes mellitus. J. Nutr. Sci. Vitaminol. 42: 517–526.

Zhang, H., et al. (1997) Biotin administration improves the impaired glucose tolerance of streptozotocininduces diabetic Wistar rats. J. Ntr. Sci. Vitaminol. 43(3):271–280.

*Primary Examiner*—Jerome D. Goldberg
*Attorney, Agent, or Firm*—Knobbe, Martens Olson and Bear, LLP

[57] ABSTRACT

A method for treating Type II diabetes by administering to an affected individual a combination of chromic tripicolinate and biotin at doses far beyond the nutritional requirements. The two compounds are administered orally or parenterally at in daily dosages which provide between 1,000 and 10,000 μg of chromium and between 1 mg and 200 mg biotin.

10 Claims, No Drawings

HIGH-DOSE CHROMIUM/BIOTIN TREATMENT OF TYPE II DIABETES

FIELD OF THE INVENTION

The present invention relates to the treatment of adult-onset non-insulin dependent (Type II) diabetes. More specifically, the invention relates to the treatment of Type II diabetes by administering supranutritional doses of chromic picolinate and biotin.

BACKGROUND OF THE INVENTION

Diabetes mellitus is known to affect at least 10 million Americans, and millions more may unknowingly have the disease. In the form of this disease known as Type II, non-insulin dependent or adult-onset (as opposed to juvenile diabetes or Type I), the pancreas often continues to secrete normal amounts of insulin. However, this insulin is ineffective in preventing the symptoms of diabetes which include hyperglycemia, impaired carbohydrate metabolism, glycosuria and decreased insulin sensitivity. These symptoms, if left untreated, often lead to severe complications.

Current drugs used for managing Type II diabetes fall within two classes of compounds: the biguanides and the sulfonylureas. The biguanides, e.g. metformin, are believed to prevent excessive hepatic gluconeogenesis. The sulfonylureas, e.g. tolbutamide and glyburide, lower plasma glucose primarily by stimulating insulin secretion, by enhancing insulin effects in some target tissues and by inhibiting hepatic glucose synthesis.

U.S. Pat. No. 4,315,927 discloses that when selected essential metals are administered to mammals as exogenously synthesized coordination complexes of picolinic acid, they are directly available for absorption without competition from other metals. These complexes are safe, inexpensive, biocompatible and easy to produce.

U.S. Pat. No. 5,087,623 describes the administration of chromic tripicolinate for the treatment of Type II diabetes in doses which provide between 50 and 500 μg of chromium. The U.S. Recommended Daily Allowance for chromium is 50–200 μg. Although a small decrease in glycosylated hemoglobin, an accurate indicator of blood glucose levels, was observed, the 10.4% value obtained after chromic tripicolinate treatment was still will within the diabetic range.

International Patent Application No. PCT/US96/06493 discloses the administration of high ("supranutritional") doses of chromium (1,000 to 10,000 μg/day) to individuals with Type II diabetes. Individuals who received 1,000 μg chromium per day as chromic tripicolinate exhibited a 30% decrease in glycosylated hemoglobin and a similar reduction in fasting and postprandial glucose levels.

Biotin is the prosthetic group for a number of carboxylation reactions, the most notable being pyruvate carboxylase which is involved in gluconeogenesis and replenishment of the citric acid cycle, and acetyl CoA carboxylase which plays a role in fatty acid biosynthesis. The safe and adequate recommended daily intake of biotin is 100–300 μg, although no side effects or toxicities were noted in previous clinical studies with oral biotin intakes of up to 200 mg daily (Mock et al, in *Present Knowledge in Nutrition*, seventh edition, Ziegler, E. et al., eds., ILSI Press, Washington, D.C., 1996, pp. 220–235). Supranutritional doses of biotin have been shown to have therapeutic utility in diabetes. High-dose oral or parenteral biotin has been shown to improve oral glucose tolerance in diabetic KK mice (Reddi et al., *Life Sci.*, 42:1323–1330, 1988), rats made diabetic by injection with *streptozotocin* (Zhang et al., 16th International Congress of Nutrition, Montreal, 1997, abstract book, p. 264) and in pre-diabetic Otsuka Long-Evans Tokushima Fatty rats (Zhang et al., *J. Nutr. Sci. Vitaminol.* 42:517–526, 1996).

In a clinical study, Coggeshall et al. (*Ann. N.Y. Acad. Sci.*, 447:387–392, 1985) demonstrated that a daily oral dose of biotin of 16 mg lowered fasting plasma glucose levels in Type I diabetics in whom insulin injections had been temporarily discontinued. Maebashi et al. (*J. Clin. Biochem. Nutr.* 14:211–218, 1993) showed that administration of 3 mg biotin three times per day to poorly-controlled type II diabetics resulted in improved pancreatic beta cell function as evidenced by the fact that fasting insulin levels did not decline in biotin-treated subjects despite the sharp decline in glucose levels.

There is a constant need for effective treatments for type II diabetes. The present invention addresses this need by providing a safe, inexpensive, drug-free therapeutic agent.

SUMMARY OF THE INVENTION

One embodiment of the present invention is a method for reducing hyperglycemia and stabilizing the level of serum glucose comprising administering to an individual in need thereof between about 1,000 and 10,000 micrograms per day of chromium as synthetic chromic tripicolinate in combination with between about 1 mg and 200 mg per day of biotin. Preferably, the amount of chromium administered as synthetic chromic tripicolinate is between 1,000 and 5,000 micrograms per day. Advantageously, the amount of biotin administered per day is between about 5 mg and 50 mg. In one aspect of this preferred embodiment, the chromic tripicolinate is in a pharmaceutically acceptable carrier. In another aspect of this preferred embodiment, the biotin is in a pharmaceutically acceptable carrier. Preferably, the biotin is orally administered. Advantageously, the chromic tripicolinate is orally administered. Preferably, the chromic tripicolinate is parenterally administered. In another aspect of this preferred embodiment, the biotin is parenterally administered.

The present invention also provides a pharmaceutical composition comprising chromium as synthetic chromic tripicolinate and biotin, wherein the ratio of chromium to biotin is between about 100:1 and 5:1 (w/w).

DETAILED DESCRIPTION OF THE PREFERRED EMBODIMENTS

The present invention includes the discovery that high doses of chromium, administered in the form of chromic picolinate, about an order of magnitude higher than the U.S. RDA, combined with high doses of biotin, promote significant reduction in blood glucose levels and stabilize blood glucose levels in individuals with type II diabetes. This reduction is markedly greater than what would be expected when either component is administered alone, thus indicating a synergistic effect.

The synthesis of chromic picolinates is described in U.S. Pat. No. 5,087,623, the entire contents of which are hereby incorporated by reference. Chromic tripicolinate and biotin are commercially available from health food stores, drug stores and other commercial sources. In order to reduce the requirement for insulin and/or diabetic drugs and to reduce several important risk factors associated with Type II diabetes, it is anticipated that the dosage range of chromium administered to a patient in the form of chromic tripicolinate will be between about 1,000 and 10,000 μg/day. In a preferred embodiment, this amount is between about 1,000 and 5,000 μg/day. With regard to the biotin component of the combination therapy, the preferred daily dosage is between about 1 mg and 200 mg. More preferably, the daily dosage of biotin is between about 5 mg and 50 mg.

For oral administration, the chromic picolinates and biotin may be provided as a tablet, aqueous or oil suspension, dispersible powder or granule, emulsion, hard or soft capsule, syrup or elixir. Compositions intended for oral use may be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing chromic tripicolinate in admixture with non-toxic pharmaceutically acceptable excipients suitable for tablet manufacture are acceptable. Pharmaceutically acceptable means that the agent should be acceptable in the sense of being compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the chromic tripicolinate complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

The chromic tripicolinate preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid may likewise be used in the preparation of injectable preparations.

The pharmaceutical compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

The amount of chromic tripicolinate/biotin that may be combined with the carrier material to produce a single dosage form will vary depending upon the host treated and the particular mode of administration.

The above description of the invention is set forth solely to assist in understanding the invention. It is to be understood that variations of the invention, including all equivalents now known or later developed, are to be considered as falling within the scope of the invention, which is limited only by the following claims.

What is claimed is:

1. A method for reducing hyperglycemia and stabilizing the level of serum glucose comprising administering to an individual in need thereof between about 1,000 and 10,000 micrograms per day of chromium as synthetic chromic tripicolinate in combination with between about 1 mg and 200 mg per day of biotin, wherein the amounts of chromic tripicolinate and biotin are selected together to provide a greater than additive effect.

2. The method of claim 1, comprising administering between about 1,000 and 5,000 micrograms per day of chromium as synthetic chromic tripicolinate.

3. The method of claim 1, comprising administering between about 5 mg and 50 mg biotin per day.

4. The method of claim 1, wherein said chromic tripicolinate is in a pharmaceutically acceptable carrier.

5. The method of claim 1, wherein said biotin is in a pharmaceutically acceptable carrier.

6. The method of claim 1, wherein said chromic tripicolinate is orally administered.

7. The method of claim 1, wherein said biotin is orally administered.

8. The method of claim 1, wherein said chromic tripicolinate is parenterally administered.

9. The method of claim 1, wherein said biotin is parenterally administered.

10. A pharmaceutical composition comprising chromium as synthetic chromic tripicolinate and biotin, wherein the ratio of chromium to biotin is between about 100:1 and 5:1 (w/w) wherein the amounts of chromic tripicolinate and biotin are selected together to provide a greater than additive effect.

* * * * *